US006927223B1

(12) United States Patent
Meadows et al.

(10) Patent No.: US 6,927,223 B1
(45) Date of Patent: Aug. 9, 2005

(54) USE OF SEROTONIN AGENTS FOR ADJUNCT THERAPY IN THE TREATMENT OF CANCER

(75) Inventors: Gary G. Meadows, Pullman, WA (US); Tanja Obradovic, Dresher, PA (US)

(73) Assignee: Washington State University Research Foundation, Pullman, WA (US)

(*) Notice: Subject to any disclaimer, the term of this patent is extended or adjusted under 35 U.S.C. 154(b) by 238 days.

(21) Appl. No.: 09/866,458

(22) Filed: May 25, 2001

Related U.S. Application Data
(60) Provisional application No. 60/207,675, filed on May 26, 2000.

(51) Int. Cl.[7] .................... A01N 43/40; A61K 31/445
(52) U.S. Cl. .................. 514/321; 367/468; 367/538; 367/553; 367/647; 367/649; 367/657
(58) Field of Search ................ 514/321, 367, 514/468, 538, 647, 649, 657

(56) References Cited

U.S. PATENT DOCUMENTS

| | | | |
|---|---|---|---|
| 3,561,444 A | 2/1971 | Boucher | |
| 3,703,173 A | 11/1972 | Dixon | |
| 4,051,842 A | 10/1977 | Hazel et al. | |
| 4,140,122 A | 2/1979 | Kuhl et al. | |
| 4,383,529 A | 5/1983 | Webster | |
| 4,624,251 A | 11/1986 | Miller | |
| 4,635,627 A | 1/1987 | Gam | |
| 4,962,091 A | 10/1990 | Eppstein et al. | |
| 5,560,922 A | 10/1996 | Chlen et al. | |
| 5,859,065 A | * 1/1999 | Brandes ................ | 514/651 |
| 5,879,712 A | 3/1999 | Bomberger et al. | |

FOREIGN PATENT DOCUMENTS

WO    WO-94/07529    4/1994

OTHER PUBLICATIONS

Abdul et al., Journal of Urology, vol. 154, pp 247–250, Jul., 1995.*
Carter et al., Chemotherapy of Cancer, Second Edition, 1981, John Wiley & Sons, N.Y., N.Y., pp 362–365.*
Abdul, M.,et al., "Growth–Inhibitory Effects of Serotonin uptake Inhibitors on Human Prostate Carcinoma Cell Lines", *The Journal of Urology*, 154, (1995), pp. 247–250.
Brandes, L.J., et al., "Stimulation of Malignant Growth in Rodents by Antidepressant Drugs at Clinically Relevant Doses," *Cancer Research*, 52, (1992), pp. 3496–3800.
Iken, K.et al., "Serotonin Upregulates Mitogen–Stimuilated B Lymphocyte Proliferation through 5–HT1A Receptors", *Cellular Immunology*, 163, (1995), pp. 1–9.
Joki, T., et al., "Continuous release of endostatin from microencapsulated engineered cells for tumor therapy", *Nature Biotechnology*, 19, (Jan. 2001), pp. 35–39.
Liu, Y., et al., "Haloperidol and Spiperone potentiate murine splenic B cell proliferation", *Immunopharmacology*, 34, (1996), pp. 147–159.
Merzak, A., et al., "Expression of serotonin receptors in human fetal astrocytes and glioma cell lines: a possible role in glioma cell proliferation and migration", *Molecular Brain Research*, 41, (1996), pp. 1–7.
Newman, S.P., "Chapter 9: Therapeutic aerosols", *In: Aerosols and the Lung: Clinical and Experimental Aspects*, Stewart W. Clarks, et al., Eds. Butterworth (Publisher), (1984), pp. 197–224.

(Continued)

Primary Examiner—Christopher S. F. Low
Assistant Examiner—Amy Lewis
(74) *Attorney, Agent, or Firm*—Schwegman, Lundberg, Woessner & Kluth, P.A.

(57) ABSTRACT

The invention provides a method for the treatment of cancer comprising administering a serotonin agent. Also provided is a method for the treatment of cachexia comprising administering a serotonin agent.

12 Claims, 11 Drawing Sheets

OTHER PUBLICATIONS

Pakala, R., et al., "Effect of Serotonin, Thromboxane A2, and Specific Receptor Antagonists on Vascular Smooth Muscle Cell Proliferation", *Circulation*, 96(7), (1997), pp. 2280–2286.

Sheehan, P.F.J.,et al., "Effects of Histamine and 5–Hydroxytryptamine on the Growth Rate of Xenografted Human Bronchogenic Carcinomas", *Clinical and Experimental Pharmacology and Physiology*, 23, (1998), pp. 465–471.

Steingart, A.B., et al., "Do Antidepressants Cause, Promote, or Inhibit Cancers", J. Clin. Epidemiol., 48( 11), (1995), pp. 1407–1412.

Uehara, Y. et al., "Antiproliferative Effects of the Serotonin Type 2 Receptor Antagonist, Ketanserin, on Smooth Muscle Cell Growth in Rats", *Journal of Cardiovascular Pharmacology*, 17 (Suppl. 2), (1991), pp. S154–S156.

Westphal, R.S.,et al., "Differences in Agonist–Independent and –Dependent 5–Hydroxytryptamine2C Receptor–Mediated Cell Division", *Molecular Pharmacology*, 49, (1996), pp. 474–480.

Young, M.R.I., et al., "Stimulation of splenic T–lymphocyte function by endogenous serotonin and by low–dose exogenous serotonin", *Immunology*, 80, (1993), pp. 395–400.

Zachrisson, K.,et al., "Serotonin and neuroendocrine peptides influence DNA synthesis in rat and human small intestinal cells in vitro", *Acta Physiol. Scand.163*, (1998), pp. 195–200.

\* cited by examiner

USE OF SEROTONIN AGENTS FOR ADJUNCT THERAPY IN THE TREATMENT OF CANCER

PRIORITY OF INVENTION

This application claims priority of invention from U.S. Provisional Application No. 60/207,675 filed on 26 May 2000.

STATEMENT OF GOVERNMENT RIGHTS

This invention was made with grants from the Government of the United States of America (grants T32AA07557 and ROIAA07293) from the National Institutes of Health. The Government may have certain rights in the invention.

FIELD OF THE INVENTION

This invention relates to the use of serotonin agents in the treatment of malignancies. More specifically, this invention relates to the use of agents that affect serotonin neurotransmission, e.g., serotonergic agents, serotonin reuptake inhibitors and selective serotonin reuptake inhibitors, to inhibit the growth of tumors and maintain the body weight of patients with cancer, e.g., melanoma. More specifically, this invention relates to the use of selective serotonin reuptake inhibitors (SSRIs), e.g., fluoxetine, for adjunct therapy in the treatment of melanomas.

BACKGROUND OF THE INVENTION

Cancer is a general term frequently used to indicate any of the various types of malignant neoplasms (i.e., abnormal tissue that grows by cellular proliferation more rapidly than normal), most of which invade surrounding tissue, may metastasize to several sites, are likely to recur after attempted removal, and causes death unless adequately treated. Stedman's Medical Dictionary, Williams & Wilkins, Baltimore, Md., 26th ed. 1995. Although a variety of approaches to cancer therapy (e.g., surgical resection, radiotherapy, and chemotherapy) have been available and commonly used for many years, cancer remains one of the leading causes of death in the world. Melanoma is a particularly deadly neoplasm. Often a late sequela of excessive exposure to sun, it is a rapidly growing tumor that metastasizes early and often. Tumor growth leads to weight loss and patients frequently experience depression. Currently, there is no effective treatment for melanoma, and most patients with metastatic disease will die prematurely.

Antidepressants are widely prescribed, not only to treat depression, but also to treat anxiety disorder, obsessive-compulsive disorder, panic, bulimia nervosa and chronic pain. It is estimated that approximately 6% of the general population and 25% of hospitalized cancer patients, who often experience anxiety and pain due to the progression of their disease, are clinically depressed.

Selective serotonin reuptake inhibitors (SSRI) agents are widely used as anti-depressants. This group of compounds includes fluoxetine, sertraline, paroxetine, fluvoxamine and citalopram. It is thought that such compounds act by inhibiting the transport of the neurotransmitter serotonin (5-hydroxytryptamine, 5-HT), thereby increasing the efficacy of neurotransmission. In addition, fluoxetine has been shown to be effective for the treatment of obsessive-compulsive disorder and bulimia nervosa.

Although serotonin is characterized as a neurotransmitter, serotonin transporters have been found in many non-neural cells, including cancer cells. Its function in non-neural cells has not been fully elucidated. However, the widespread distribution of transporters suggests that the effect of serotonergic drugs is pleiotropic and can be considered unpredictable. Medical personnel can be reluctant to prescribe anti-depressants to alleviate major depression or adjustment disorder of cancer patients, because of conflicting reports on the stimulation of cancer growth by anti-depressants. Steingart et al. reviewed the literature published from 1976 to 1993 for reports of human and experimental studies that examined the association of antidepressants with cancer or the effect of antidepressants on neoplastic growth (Steingart et al., J. Clin. Epidemiol., 48, 1407–1412 (1995)). Their search revealed four human studies and nine experimental models reported conflicting results. For example, the widely used antidepressant fluoxetine was reported to be both a tumor promoter and an antineoplastic agent.

Antidepressants are not neoplastic-causing agents per se, but may directly or indirectly promote or suppress neoplasms once established. For example, tumors contain varying levels of serotonin transporters, the binding to which by serotonin or a serotonin transport inhibitor somehow affects tumor growth. The presence of serotonergic agents may thus have a direct effect on tumor growth. Alternatively, metabolic pathways, e.g., P-450 mixed function monooxygenase system, which activate many antineoplastic drugs may be inhibited or stimulated by SSRIs, modulating the effectiveness of chemotherapeutic agents. Fluoxetine is known to bind to growth-regulatory intracellular histamine receptors and has been shown to inhibit immune function, which tends to permit tumor growth. It is suspected that the conflicting reports of tumor promotion versus suppression cited in the above review may be the result of timing of dosage, level of dosing, effect on the immune system, stage of the disease or specificity of the tumor. In any case, it is apparent that the effect of serotonergic agents is complex and unpredictable. It is necessary in each case to balance carefully the advantages and disadvantages of anti-depressant drugs for cancer patients.

Thus, there is a need to provide the psychological benefits of antidepressant therapy to cancer patients, without interfering with treatment modalities, e.g., chemotherapy, or the potentiation of tumor growth. In addition, there exists a need for effective melanoma therapies.

SUMMARY OF THE INVENTION

The present invention is directed to a method for treating cancer in a mammal, e.g., melanoma The active ingredient is an serotonin agent, i.e., an agent that affects serotonin neurotransmission, e.g., a serotonergic agent, a serotonin reuptake inhibitor (SRI) or a selective serotonin reuptake inhibitor (SSRI) such as fluoxetine, and can be given orally, subcutaneously, topically or injected into the tumor. An agent of the invention can be administered in conjunction with chemotherapy, biological therapy, or radiotherapy. The present invention is also directed to a method for inhibiting the growth of a cancer cell, for example, a melanoma cell, e.g., a pigmented cell or a non-pigmented cell, by the administration of a serotonin agent. The invention is also directed to ameliorating cachexia, e.g., weight loss, and depression that are frequently experienced by patients suffering from melanoma by administering a serotonin agent, e.g., a SSRI.

DETAILED DESCRIPTION OF THE INVENTION

I. Definitions

Figure 1:
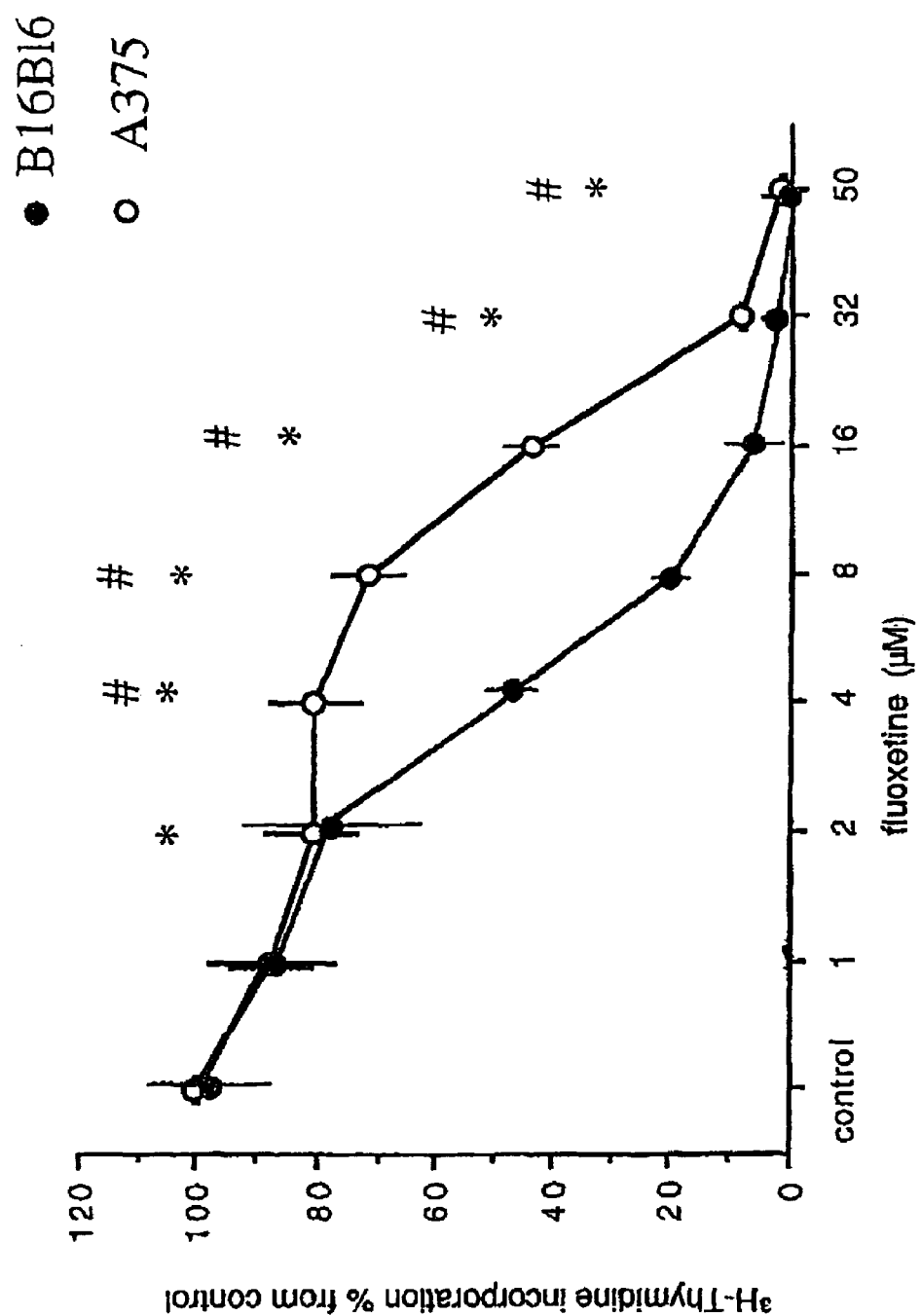
FIG. 1 shows the dose-dependent inhibition of proliferation by fluoxetine of B16BL6 and A375 melanoma cells in vitro by fluoxetine as measured by incorporation of tritiated thymidine. #Different from untreated cells, p<0.05. *Different from A375 cells, p<0.05.

As used herein, a "serotonin agent" refers to an agent that directly or indirectly affects serotonin neurotransmission. For example, a serotonin agent can be an agonist or an antagonist of a serotonin receptor and/or transporter. In addition, a serotonin agent can be a "serotonergic agent", i.e., an agent that affects the activity and/or the availability of serotonin and/or its precursor, L-typtophan, or a serotonin reuptake inhibitor (SRI), i.e., an agent having some serotonin reuptake inhibitor activity but not specific for serotonin, or a serotonin and norepinephrine reuptake inhibitor (SNRI), e.g., venlafaxine. Preferably, a serotonin agent of the invention is a "selective serotonin reuptake inhibitor (SSRI)". A "selective serotonin reuptake inhibitor (SSRI)" refers to an agent that can alter the synaptic availability of serotonin through their inhibition of presynaptic reaccumulation of neuronally released serotonin. Suitable SSRIs for use in the present invention include: fluoxetine, fluvoxamine, paroxetine, sertraline, citalopram and the pharmaceutically acceptable salts thereof. A preferred SSRI of the invention is fluoxetine and the pharmaceutically acceptable salts thereof.

By "inhibition of tumor cell growth" is meant an inhibition of tumor cell growth and/or proliferation, as well as of the migration of a tumor cell. Tumor cell growth refers to the unregulated growth, lack of differentiation, local tissue invasion, and metastasis of a cancer, i.e., malignant, cells.

As used herein, "melanoma" refers to a malignant neoplasm derived from cells that are capable of producing melanin. The term melanoma, synonymous with "malignant melanoma", includes cutaneous melanoma, ocular melanoma and intraocular melanoma. Melanoma frequently metastasizes widely, involving a patients lymph nodes, skin, liver, lungs and brain tissues.

The term "pigment cell" refers to a melanocyte. Most pigment cells are in the skin. By "non-pigment cell" is meant a non-melanocyte.

The term "chemotherapeutic agent" refers to any compound that has biological activity against one or more forms of cancer. Suitable chemotherapeutic agents include antineoplasts, e.g., adjuncts, androgen inhibitors, antibiotic derivatives, antiestrogens, antimetabolites, hormones, immunomodulators, and nitrogen mustard derivatives, as well as cytotoxic agents and steroids. See *Physicians' Desk Reference*, 51th ed. 1997.

"Biological therapy" or "immunotherapy" is a form of treatment that uses the body's immune system, either directly or indirectly, to fight cancer or to lessen side effects caused by some cancer treatments. Biological therapy is also a systemic therapy and involves the use of substances called biological response modifiers (BRMs), which include interferon-alpha and interleukin-2.

"Radiation therapy" (also called radiotherapy) refers to the use of high-energy rays to kill cancer cells.

As used herein, the term "mammal" means a warm blooded mammal, including humans, and is meant to encompass mammals in need of treatment for melanoma, especially humans; thus in some instances the term "patient" or "subject" is alternatively used for mammal.

"Cachexia" refers to the general weight loss and wasting that occurs in the course of a chronic disease, e.g., the loss of body weight and muscle mass, i.e., protein, frequently observed in patients with cancer, AIDS, or other diseases.

II. Dosages. Formulations and Routes of Administration of the Serotonin Agents of the Invention The serotonin agents of the invention, and the pharmaceutically acceptable salts thereof, are preferably administered in therapeutically effective, anti-tumor amount. To achieve this effect(s), the serotonin agents, e.g., SSRIs or pharmaceutically effective salt thereof, may be administered at dosages of at least about 0.001 to about 100 mg/kg, more preferably about 0.01 to about 50 mg/kg, and even more preferably about 0.1 to about 10 mg/kg, of body weight, although other dosages may provide beneficial results. For example, fluoxetine may be administered to a patient in a dose range between about 20mg/day to about 80 mg/day.

The amount administered will vary depending on various factors including, but not limited to, the agent(s) chosen, the weight, the physical condition, and the age of the mammal, and whether prevention or treatment is to be achieved. Such factors can be readily determined by the clinician employing animal models or other test systems which are well known to the art.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

A serotonin agent, e.g., a SSRI, may be administered alone, with other anti-cancer agents, e.g., in combination with traditional chemotherapy, radiotherapy, and/or biologic therapy agents.

Thus, one or more suitable unit dosage forms comprising the therapeutic agents of the invention, which, as discussed below, may optionally be formulated for sustained release. For example, the unit dosage forms of the invention may be formulated using microencapsulation, see WO 94/07529, and U.S. Pat. No. 4,962,091 the disclosures of which are incorporated by reference herein. Materials for microencapsulation include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. Preferred carriers are polysaccharides such as hyaluronic acid, sodium alginate and dextran sulfate. More preferably, a therapeutic agent of the invention is encapsulated in alginate beads. See, for example, U.S. Pat. No. 5,879,712.

Alginates also have been used in fluid suspensions for many years because of their ability to form a gel upon contact with gastric fluids. Alginate is a collective term for a family of copolymers containing 1,4-linked-D-mannuronic and -L-guluronic acid residues in varying proportions and sequential arrangement. Alginate forms gels with divalent ions like calcium, and the gel-forming properties are strongly correlated with the proportion and lengths of the blocks of contiguous L-guluronic acid residues in the polymeric chains. Preferred sustained release dosage forms comprise a serotonin agent of the invention, e.g., a SSRI encapsulated in alginate beads (see, for example, Joki et al., *Nat. Biotech.*, 19, 35 (2001)).

Thus, the unit dosage forms comprising the therapeutic agents of the invention can be administered by a variety of routes including oral, or parenteral, including by rectal, transdermal, subcutaneous, intravenous, intramuscular, intraperitoneal, intrathoracic, intrapulmonary and intranasal (respiratory) routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. Preferably, orally administered therapeutic agents of the invention are formulated for sustained release, e.g., the agents are microencapsulated. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the therapeutic agents of the invention can be prepared by procedures known in the art using well-known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets of an agent of the invention are designed to resist disintegration in the stomach and dissolve in the more neutral to alkaline environment of the duodenum.

The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, C1–C4 alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and alpha-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles or waxes. These coatings, envelopes, and protective matrices are useful to coat indwelling devices, e.g., stents, catheters, peritoneal dialysis tubing, and the like. Preferably, the peptides are formulated as microspheres or nanospheres.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polyrnethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For topical administration, the therapeutic agents may be formulated as is known in the art for direct application to a target area. Conventional forms for this purpose include wound dressings, coated bandages or other polymer coverings, ointments, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1–25% by weight.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The agent may be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific indication or disease. Any statistically significant attenuation of one or more symptoms of an indication or disease that has been treated pursuant to the method of the present invention is considered to be a treatment of such indication or disease within the scope of the invention.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0–8.0. saline solutions and water.

The agents of the present invention can be administered as a dry powder or in an aqueous solution. Preferred aerosol pharmaceutical formulations may comprise, for example, a physiologically acceptable buffered saline solution containing between about 0.1 mg/ml and about 100 mg/ml of one or more of the agents of the present invention specific for the indication or disease to be treated.

Dry aerosol in the form of finely divided solid peptide or nucleic acid particles that are not dissolved or suspended in a liquid are also useful in the practice of the present invention. Peptide or nucleic acid may be in the form of dusting powders and comprise finely divided particles having an average particle size of between about 1 and 5 m, preferably between 2 and 3 m. Finely divided particles may be prepared by pulverization and screen filtration using techniques well known in the art. The particles may be administered by inhaling a predetermined quantity of the finely divided material, which can be in the form of a powder.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator, or a metered-dose inhaler (see, for example, the pressurized metered dose inhaler (MDI) and the dry powder inhaler disclosed in Newman, S. P. in Aerosols and the Lung, Clarke, S. W. and Davia, D. eds., pp. 197–224, Butterworths, London, England, 1984).

Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.).

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

The formulations and compositions described herein may also contain other ingredients such as antimicrobial agents, or preservatives. Furthermore, the active ingredients may also be used in combination with other therapeutic agents, for example, bronchodilators.

Preferred delivery systems for a peptide can include coupling the peptide to a carrier or an intact attenuated microbe, such as an inactivated virus or attenuated bacterium, e.g., weakened *Salmonella*, preparing a multiple antigen peptide, using liposomes or other immunostimulating complexes. Preferably, the delivery system enhances the immunogenicity of the peptide. Preferred carrier proteins include large antigenic proteins such as DTD and TTD, or a fusion protein having a carrier protein of bacterial, e.g., *Salmonella flagellin*, or viral origin. Viral vectors that may be employed to deliver nucleic acid encoding the peptide include, but are not limited to, retroviral vectors, vaccinia virus vectors, adenovirus vectors or canarypox virus vectors.

The invention will be described with reference to the following non-limiting examples.

EXAMPLE 1

Effect of Fluoxetine on Melanoma Proliferation In Vitro

It has been previously reported that fluoxetine stimulated the growth of melanomas in mice bearing inoculated melanoma cells (Brandes et al., *Cancer Research*, 52, 3796–3800 (1992)). Brandes et al., 1992, injected B16F10 melanoma cells i.v. into the tail veins of mice, which caused death from multiple pulmonary tumors (median survival, 16–17 days). Twenty-four hours following tumor cell inoculation, all animals were injected with saline (control), or fluoxetine or amitriptyline as test agents. Amitriptyline was administered at 30, 60, or 75 mg/m$^2$. Fluoxetine was administered at 12, 16, 20 or 40 mg/m$^2$. Both test agents caused increased tumor lung colonization as determined by wet weight of tumor aggregates, as compared to the saline controls, although all groups had a median survival of 17 days when the tumor cells were injected i.v.

In order to estimate whether lower doses of fluoxetine may be suitable for in vivo studies, an in vitro dose-dependent relationship was determined. Two different melanoma cell lines, B16BL6 and A375, were evaluated for proliferation in the presence or absence of fluoxetine.

As shown in FIG. 1, fluoxetine at physiologically relevant levels surprisingly did not increase tumor growth as found by Brandes et al., 1995 but actually inhibited the growth of B16BL6 and A375 melanoma cells in vitro as measured by the incorporation of tritiated thymidine. Levels between 4 and 15 uM fluoxetine caused 50% inhibition, while levels of about 30 uM completely inhibited the incorporation of isotope.

EXAMPLE 2

In vivo Inhibition of Tumor Growth

In an effort to approximate the effect of SSRIs on melanomas in clinical situations, administration of the agents began after tumor growth was apparent. The fluoxetine dose chosen, 10 mg/kg/day, when injected i.v. or continuously infused subcutaneously via pump gives an approximate serum level of 100–280 ng/ml in mice. Thus, the fluoxetine level used in the studies reported herein is most likely lower than that observed in depressed patients taking fluoxetine.

Fourteen to 16 C57BL6 mice per group were inoculated s.c. with 1×10$^6$ B16BL6 melanoma cells. At 14 days, all mice had developed subcutaneous tumors, at which point fluoxetine or saline was administered by injection. The test agent and saline control were injected daily subcutaneously (s.c.) into the gluteal region opposite from the site of tumor inoculation, approximately two hours before the dark cycle. During this period, fluoxetine administration significantly (p<0.05) decreased tumor volume in both water- and ethanol-consuming mice. At 21 days the animals were sacrificed.

Figure 2:
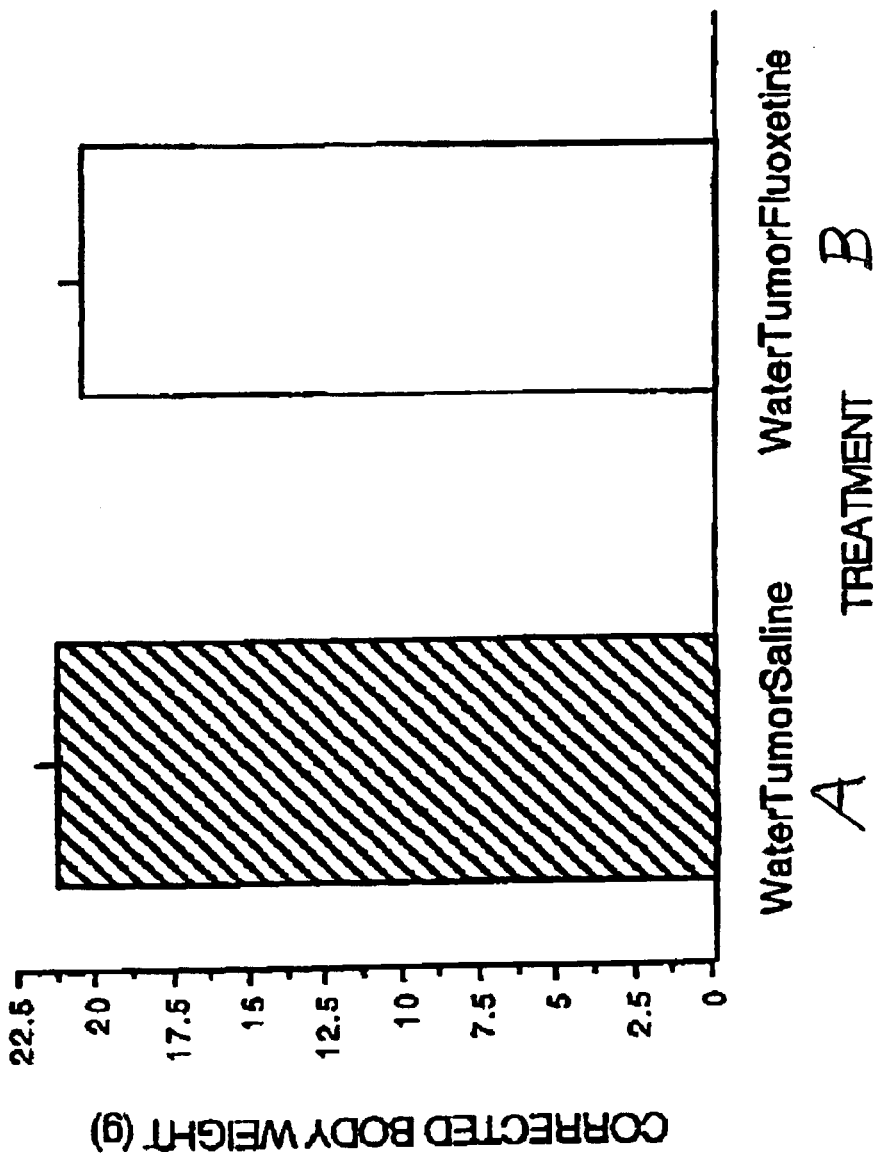
FIG. 2 shows the corrected body weight of mice inoculated with melanoma cells.

As shown in FIG. 2, the corrected body weight of the control and test animals was nearly identical. The corrected body weight was determined by subtracting the wet weight of the tumor from the total body weight of each animal. The animals given fluoxetine showed a greater than 2-fold decrease in the wet weight of tumors as determined at necropsy. In addition the number and frequency of metastases was greatly reduced.

EXAMPLE 3

Prevention of Body Weight and Fat Loss

One of the clinical effects of cancer is wasting, also referred to as cachexia. The loss of body weight and particularly fat due to the voracious metabolism of the tumor and also to toxic metabolites produced contributes to the general malaise that accompanies cancer and, in addition, to decreased quality of life and may contribute to earlier death. Previously, it was demonstrated that ethanol consumption augmented fat loss in mice inoculated subcutaneously into the dorsal hip with B16BL6 melanoma. To determine if fluoxetine could (i) inhibit tumor growth in mice with established B16BL/6 melanoma in vivo and (ii) prevent the loss of body fat during ethanol consumption, the effect of a low dosage of fluoxetine administered with and without ethanol to tumor-bearing mice was examined.

Methods

Female C57/BL6 mice consumed either water or 20% w/v ethanol ad libitum for six weeks prior to inoculation with of melanoma cells. The mice were injected with 1×10$^6$ tumor cells subcutaneously (s.c.) into the dorsal hip.

Two weeks after inoculation, the animals were divided into four treatment groups: (1) water drinking or (2) ethanol drinking, both groups injected with saline control for seven days; (3) water drinking or (4) ethanol drinking. Both groups were then administered daily subcutaneous injections of 10 mg/kg/day of fluoxetine or an equivalent volume of normal saline for 7 days. Tumor growth was measured with calipers on days 14, 16, 18, and 20. Mice were killed on day 21 and necropsied.

Perigonadal and carcass fat were determined. Body weight, food consumption, and fluid-consumption were measured continually throughout the experiment.

Results

Figure 3:
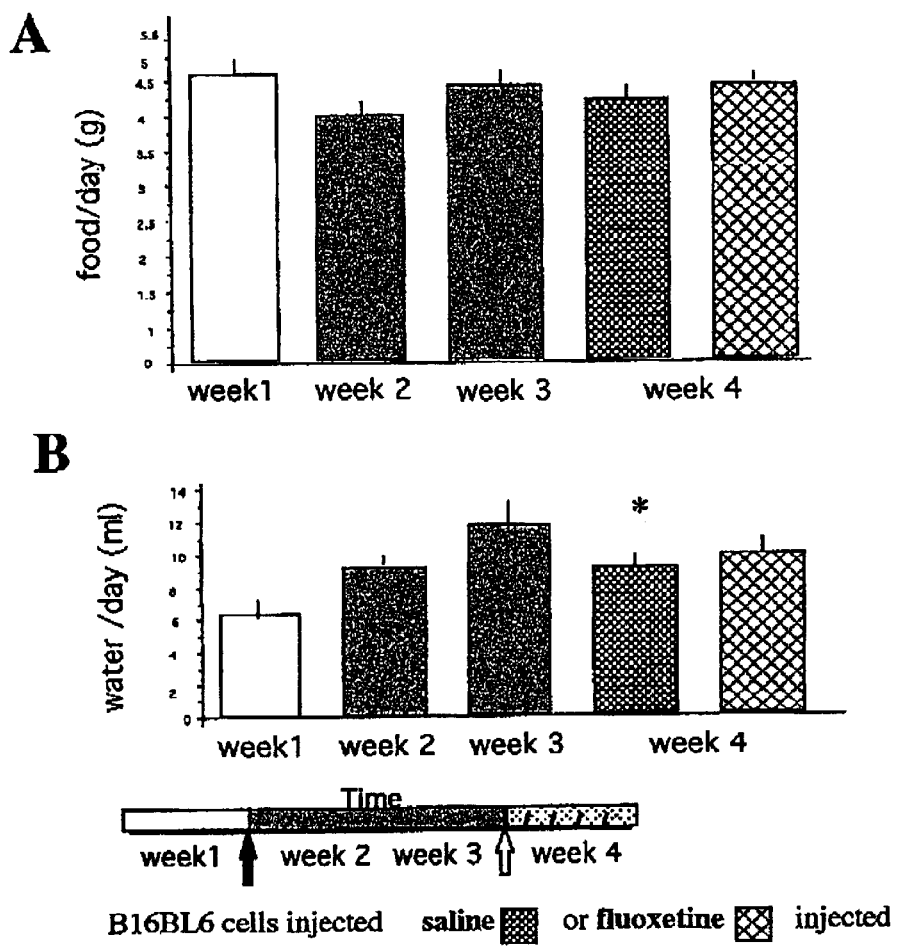
FIG. 3 shows the weekly food (A) and water (B) consumption in mice inoculated with fluoxetine and B16BL6 melanoma. *Different from intake during the third treatment week (second week of tumor growth) p<0.05.

FIG. 3A shows that fluoxetine treatment does not alter food intake during the experimental period. Water intake was slight decreased on week 4 relative to week three, however the intake was not different from other time periods (FIG. 3B). These data indicate that fluoxetine treatment did not have a negative effect on the nutritional status of the mice.

Figure 4:
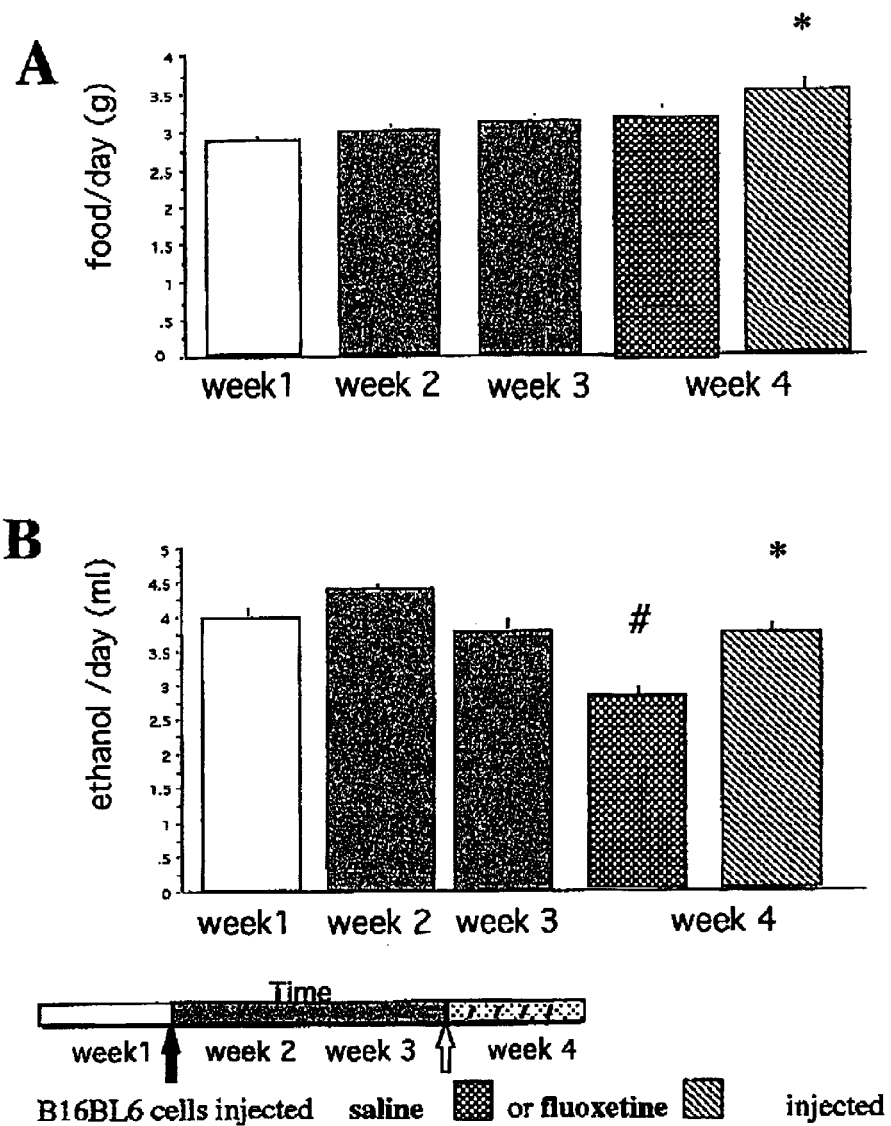
FIG. 4 shows the weekly food (A) and ethanol (B) consumption in mice inoculated with fluoxetine and B16BL6 melanoma. *Different from saline-injected group, p<0.01. #Different from intake during third treatment week (second week of tumor growth), p<0.01.

FIG. 4A shows that fluoxetine actually stimulated food intake in the ethanol consuming mice during the treatment period. FIG. 4B shows that ethanol intake decreased during the fourth week after tumor inoculation in the saline injected group, but not in the group injected with fluoxetine. The fluoxetine effect on ethanol intake was not due to change in consumatory behavior since the water drinking mice injected with saline or fluoxetine consumed equal amounts of water.

Figure 5:
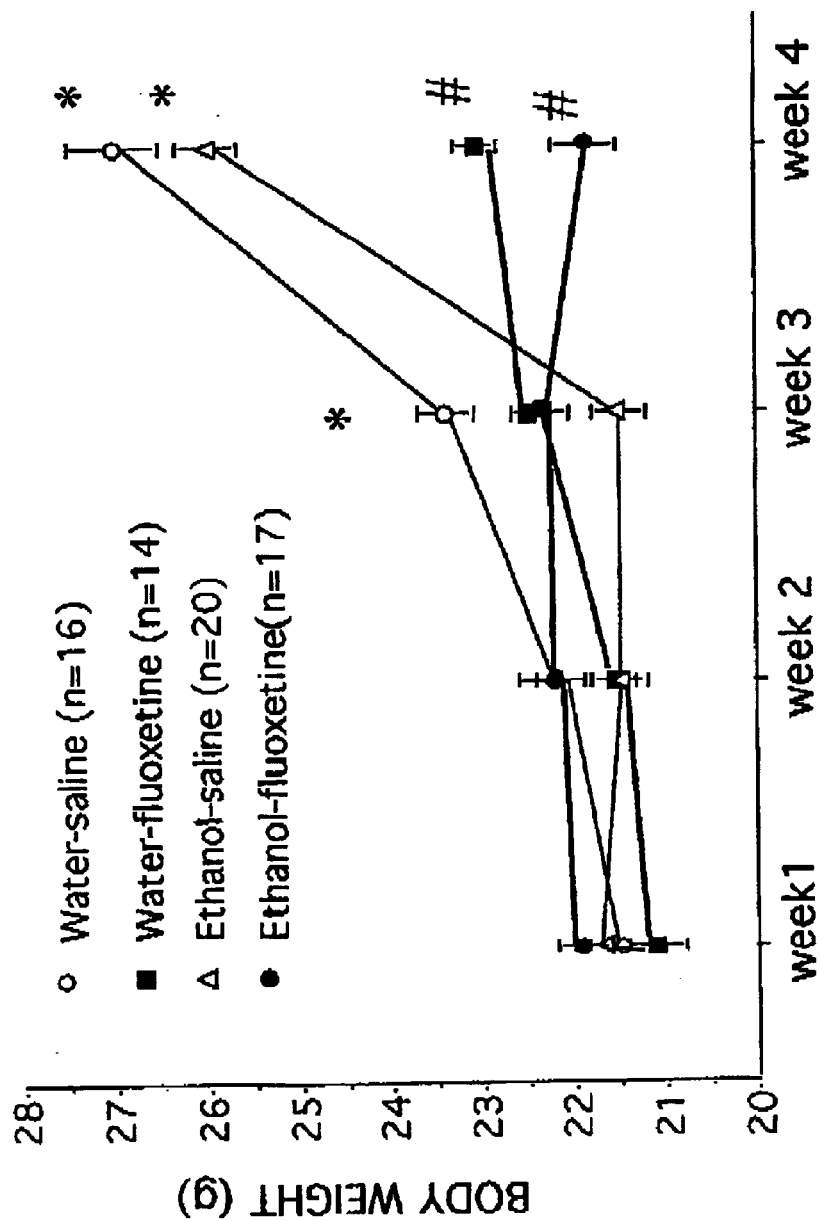
FIG. 5 shows the body weight changes in water-drinking and ethanol-drinking mice inoculated with B16BL6 melanoma and injected for 7 days with saline or fluoxetine beginning on week 3. *Different from all other treatment groups, p<0.05. #Different from all other treatment groups, p<0.01.

The average weekly body weight of mice in all four treatment groups increased during tumor growth (FIG. 5). FIG. 5 shows that the mice inoculated with tumor gained body weight from week 3 to week 4 in the saline injected group irrespective of water or ethanol consumption. Mice in the fluoxetine groups, however, did not gain body weight during this time period.

Figure 6:
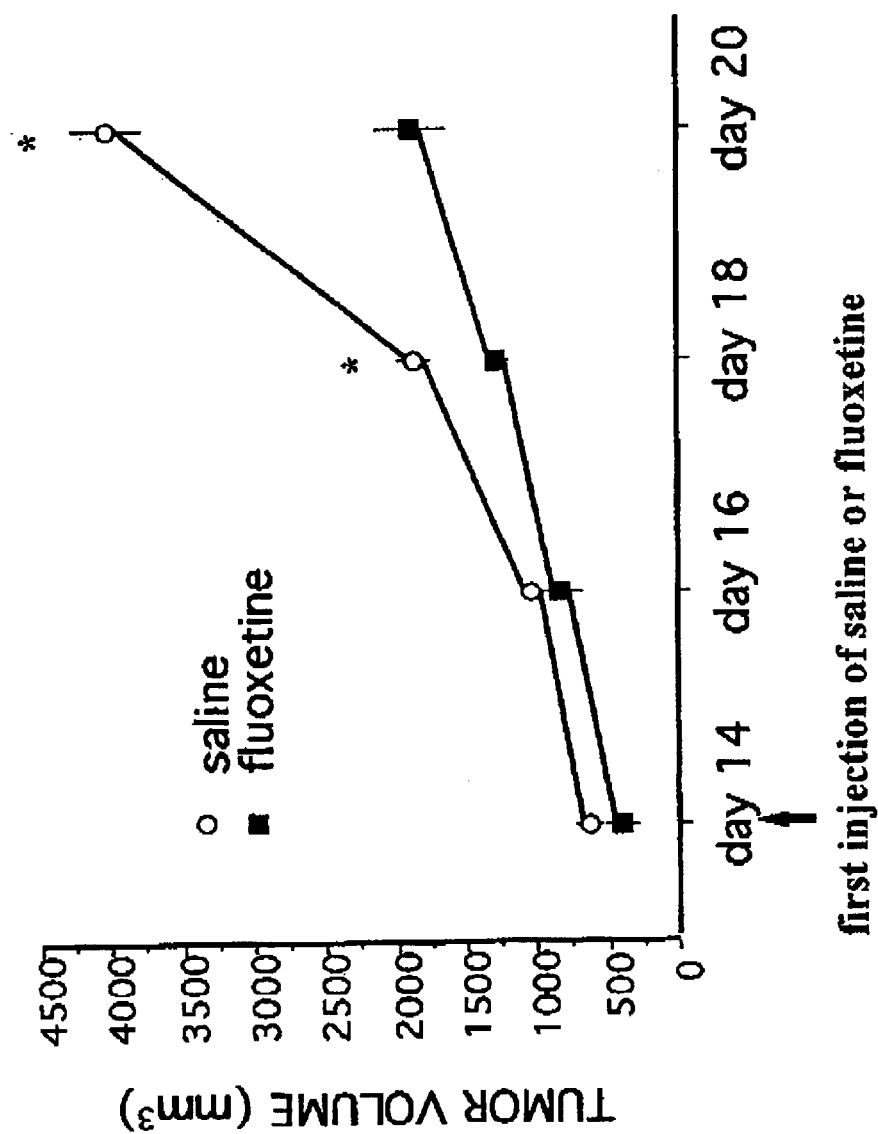
FIG. 6 shows that fluoxetine decreases the rate of tumor growth in water-consuming mice inoculated with B16BL6 melanoma. Tumors were measured with calipers and the volume calculated according to the formula for a hemielipsoid. *Different from fluoxetine injected group, p<0.05.

Fluoxetine administration to ethanol-drinking tumor-bearing mice during the third week of tumor growth caused a significant ($p<0.001$) increase in food and ethanol consumption as compared to saline-injected controls (FIGS. 5 and 6).

Figure 7:
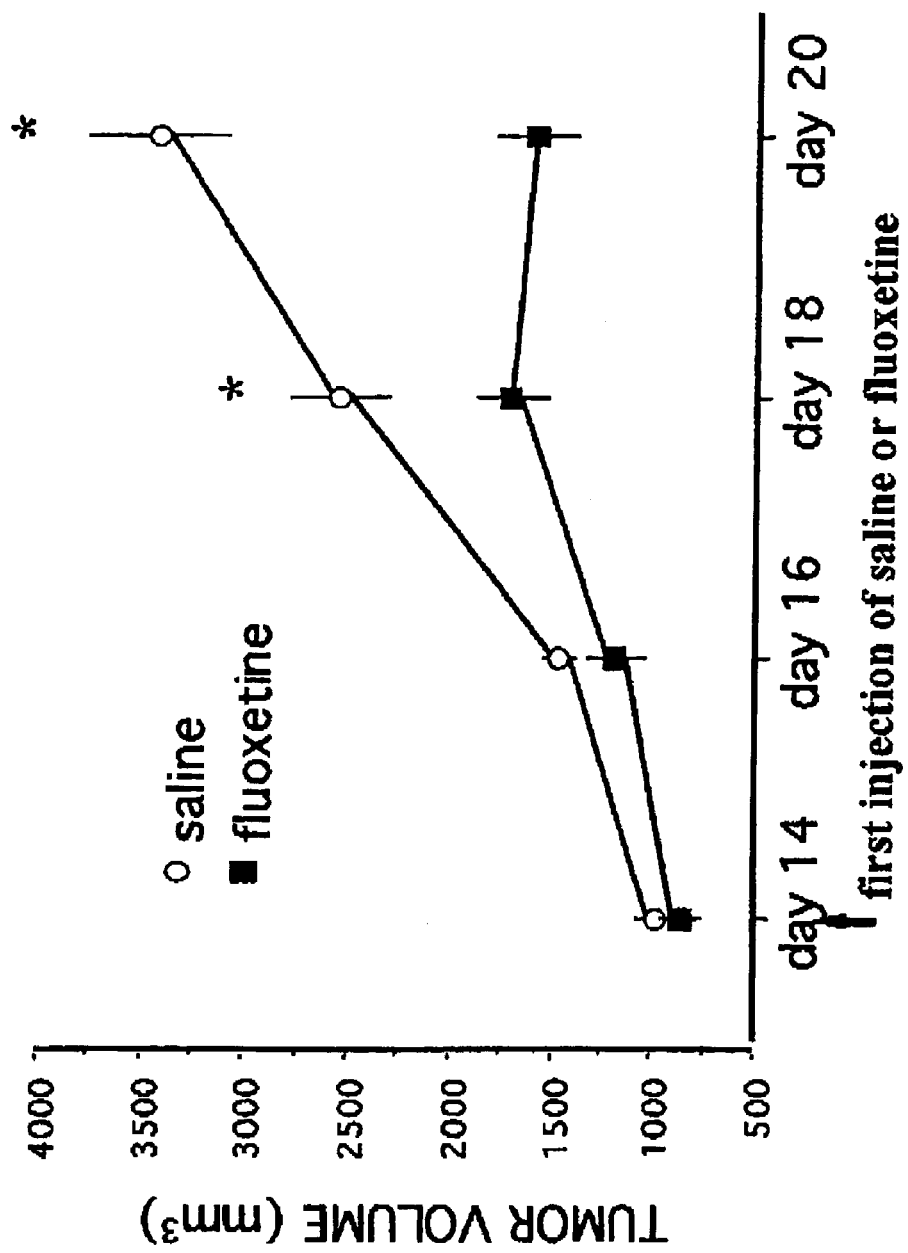
FIG. 7 shows that fluoxetine decreases the rate of tumor growth in ethanol-consuming mice inoculated with B16BL6 melanoma. Tumors were measured with calipers and the volume calculated according to the formula for a hemielipsoid. *Different from fluoxetine injected group, p<0.05.
Figure 8:
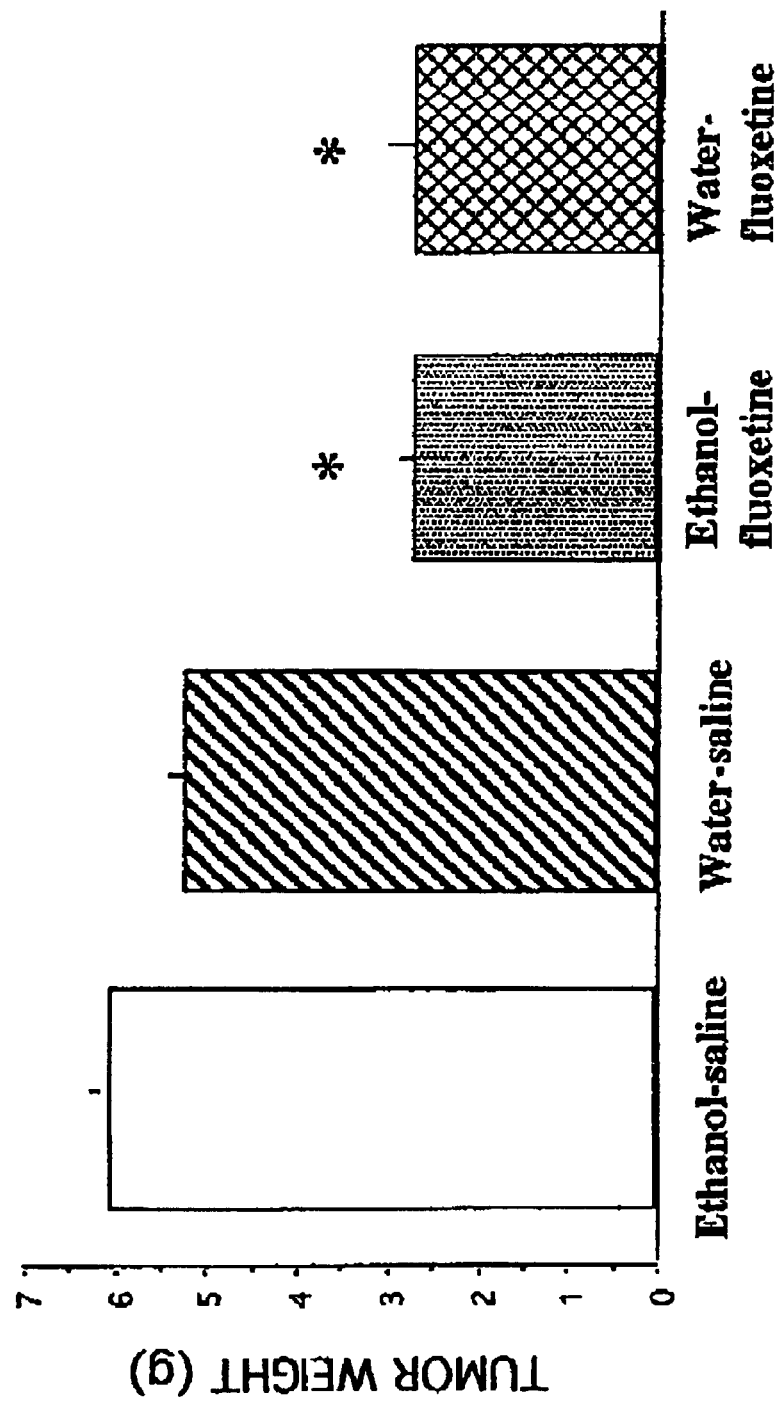
FIG. 8 shows that fluoxetine decreases final B16BL6 melanoma tumor weight at necropsy. *Different from saline-injected water- and ethanol-drinking groups, p=0.0001.

FIGS. 6 and 7 show that tumor growth rate was significantly decreased by fluoxetine treatment. The tumor growth rate was decreased irrespective of water or ethanol consumption, FIG. 8 shows that the final weight of the tumor in mice treated with fluoxetine is greater than 2-fold lower than the weight of saline-injected mice. The decrease in tumor weight explains the changes in body weight depicted in FIG. 5.

Body composition, i.e., the effect of fluoxetine on perigonadal fat and carcass lipid in water-drinking and ethanol-drinking mice inoculated with B16BL6 melanoma tumors, was analyzed (Table 1). Perigonadal fat, a measure of body fat content, was removed at necropsy and weighed. Mice were then dehydrated at 60° C. until they reached constant weight. They were then pulverized in a Bel-Art Micro-Mill. The whole carcass was transferred to a soxhlet extractor and the lipid was extracted with chloroform:methanol (2:1) for 24 hours. The extraction cone containing the carcass was removed, air-dried to evaporate the chloroform and methanol, and then weighed. The difference in weight was the weight of carcass lipid. The percentage of carcass lipid was calculated as the weight of lipid/dry carcass weight× 100.

TABLE 1

| Group | n | Perigonadal Fat (mg ± SE) | n | Carcass Fat (% ± SE) |
| --- | --- | --- | --- | --- |
| Water | | | | |
| Saline | 16 | 17 ± 6 | 10 | 26.1 ± 2.1 |
| Fluoxetine | 20 | 53 ± 25 | 20 | 25.8 ± 1.4 |
| Ethanol | | | | |
| Saline | 20 | 11 ± 3 | 8 | 19.7 ± 1.6* |
| Fluoxetine | 17 | 192 ± 53# | 16 | 31.7 ± 2.3# | n = number of mice evaluated.
*Different from Water groups, $p < 0.01$.
Different from Ethanol-Saline group, $p <0.002$. Differences were determined by Fisher's Protected LSD test.

The amount of perigonadal fat was increased following fluoxetine treatment in both water and ethanol drinking mice.

The data presented in Table 1 show that fluoxetine significantly prevented the loss in perigonadal and carcass lipid induced by ethanol consumption in melanoma-bearing mice. Fluoxetine-induced decrease in final body weight of both water and ethanol drinking tumor-bearing animals is considered to be due to the inhibitory effect of fluoxetine on tumor growth.

Figure 9:
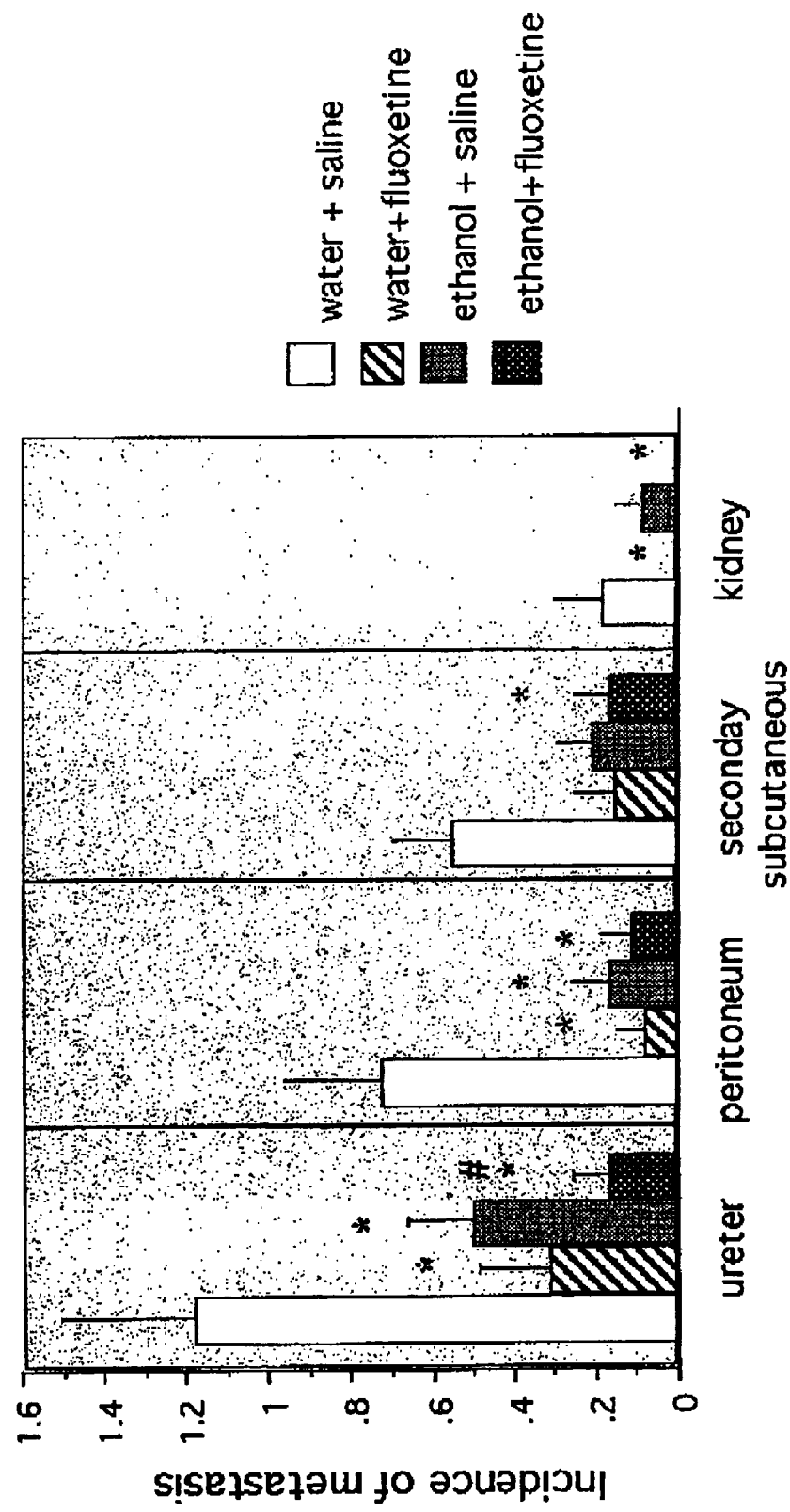
FIG. 9 shows that fluoxetine decreases metastasis from subcutaneous B16BL6 melanoma tumors. *Different from water-drinking and saline-injected groups, p<0.05. #Different from ethanol-drinking and saline-injected group, p<0.05.

FIG. 9 shows that ethanol and fluoxetine independently inhibit metastasis in mice bearing subcutaneous B16BL6 melanoma tumors. The effects of ethanol consumption and fluoxetine consumption similarly reduced peritoneal and secondary subcutaneous metastasis. Fluoxetine had a more pronounced effect on metastasis to the kidney, however, metastasis to this organ was low in all groups. Fluoxetine decreased metastasis to the ureter as did ethanol consumption, however there was a significant interaction between ethanol and fluoxetine and metastasis to the ureter was lowest in mice consuming ethanol and also treated with fluoxetine.

Collectively, the in vivo experiments indicate that fluoxetine therapy is effective against established melanoma tumors at a dose that is non toxic. It has the additional benefit of inhibiting the loss in body composition elicited by the tumor and it has an additional inhibitory effect on metastasis. Saline group, $p<0.002$. Differences were determined by Fisher's Protected LSD test.

EXAMPLE 4

Effects of Fluoxetine on Lipid Accumulation in 3T3 Adipocytes

Results from the in vivo study above (Example 3) indicated that fluoxetine treated animals retained body fat when inoculated with the B16BL6 melanoma tumor. This was especially evident in melanoma-bearing mice that consumed ethanol, which were previously demonstrated to lose body and carcass fat. The preservation of body fat could be due to an effect of fluoxetine on fat metabolism or fat synthesis. The effect of fluoxetine on lipid accumulation in differentiated 3T3 fibroblasts into adipocytes (fat cells) was examined.

Methods

The effect of $5\mu M$ and $10\ \mu M$ fluoxetine on fat content of adipocytes differentiated from NIH 3T3 fibroblasts was determined. 3T3 fibroblasts were grown to confluence in DMEM+10% FBS culture medium and then differentiated into adipocytes in this medium supplemented with 0.83 $\mu M$ insulin, 0.25 $\mu M$ dexamethasone, and 0.5 mM isobutylmethylxanthine with or without fluoxetine. After 10 days the lipid content was determined by staining the cells with Oil Red-O and determining the intensity of the red color in an uv spectrophotometer. Experiments were done in triplicate.

Results

Figure 10:
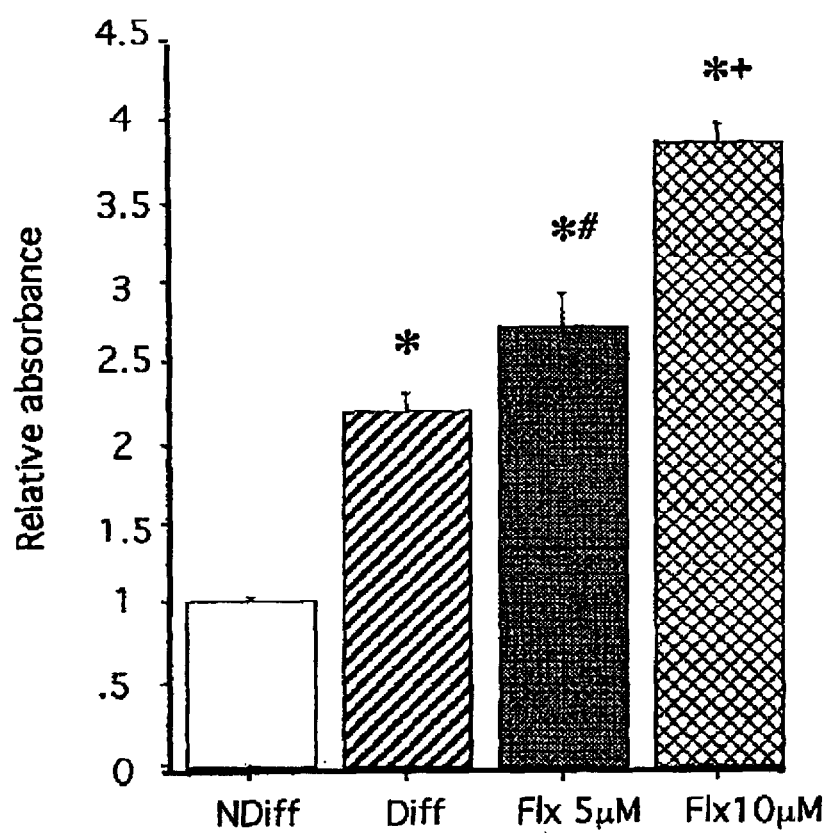
FIG. 10 shows that fluoxetine increases fat accumulation in 3T3 adipocytes. Absorbance was measured after treatment with differentiation media to which fluoxetine (Flx) was added. The relative absorbance was calculated as the ratio of absorbance of each treatment to the absorbance of the nondifferentiated (Ndiff) cells. The experiment was performed in triplicate. *Different from nondifferentiated cells, p<0.001; #Different from cells induced to differentiate without addition of fluoxetine, p<0.05; ⁺Different from cells induced to differentiate without addition of fluoxetine, p<0.001.

Fluoxetine at 5 $\mu M$ and 10 $\mu M$ increases lipid content of differentiated NIH 3T3 adipocytes (FIG. 10). Although the mechanism underlying this effect is not known, it is important to note that the concentration required to enhance lipid accumulation is lower than the cytotoxic concentration of fluoxetine on melanoma cells. See FIGS. 11 and 12.

EXAMPLE 5

Effects of Fluoxetine on Viability of Melanoma

FIG. 1 shows that fluoxetine inhibits proliferation of murine B16BL6 melanoma and human nonpigmented A375 melanoma cells. The effect was more pronounced in the murine melanoma cells. Additional studies were conducted to determine the cytotoxicity of fluoxetine in A375 melanoma cells and in human pigmented SKMel-28 cells.

Methods

The effect of fluoxetine cytotoxicity at various concentrations was determined by a crystal violet assay. A375 and SKMel-28 cells were seeded at a density of 20,000 cells in one ml DMEM+10% FBS per well in 24 well plates and cultured for 24 hours. Cells received multiple concentrations of fluoxetine for different time periods. Fluoxetine at concentrations ranging from 0, 2, 4, 8 and 16 uM were added in respective wells in quadruplicate and incubated for 24 hours, 48 hours and 72 hours at 37° C. in an humidified 5% $CO_2$ humidified incubator. The culture plates were removed and the medium from each well was discarded. The cells were fixed with acetic acid:methanol (1:3) for one hour at room temperature. The fixed cells were washed with 80% methanol and stained with crystal violet (0.5%) for one hour.

Crystal violet dye is taken up proportionately depending upon the number of cells that are adhered to the plate. Excess dye is removed by washing plates in running distilled water. After the plates were dry, the dye was solubilized in 10% acetic acid. Aliquots of solubilized dye from each well were transferred to a 96 well plate and the absorbance of the color was measured at 585 nm. The effects were compared relative to untreated controls.

Results and Conclusion

Figure 11:
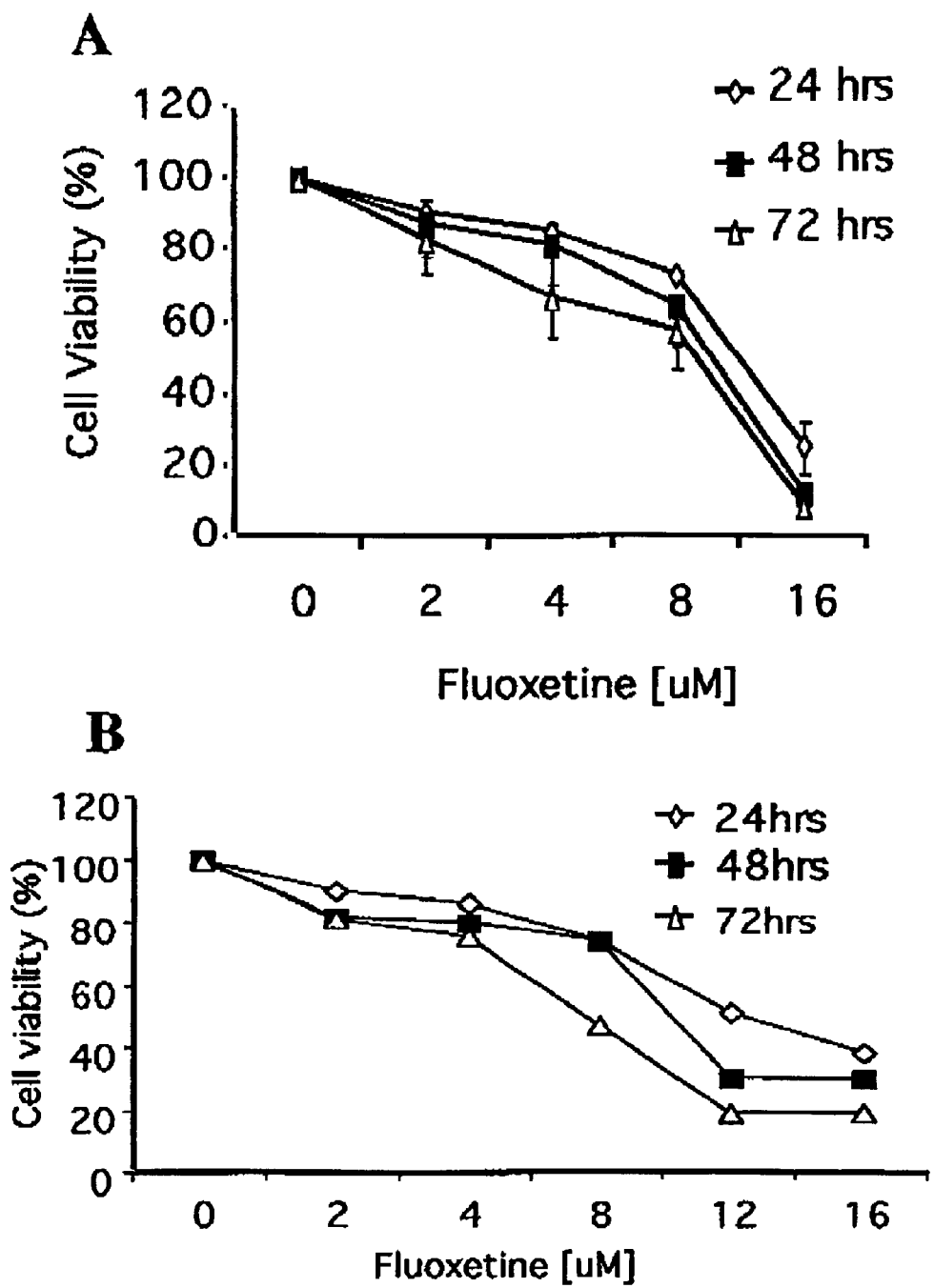
FIG. 11 shows the effect of fluoxetine concentration and time of exposure on viability of human melanoma cells. Viability was assessed by the crystal violet assay. A. Effect of fluoxetine on viability of nonpigmented A375 melanoma. Values are mean±SE for three experiments. B. Effect of fluoxetine on viability of pigmented SK-Mel 28. Values are for one experiment.

The data in FIG. 11 show that fluoxetine is cytotoxic to nonpigmented human A375 melanoma cells and to pigmented human SKMel-28 cells. Fluoxetine exerts its toxicity within 24 hr. For A375 melanoma, drug toxicity is evident at 4 $\mu$M but more pronounced from 8–16 $\mu$M. The concentration of fluoxetine that inhibited A375 viability by about 50% was approximately 12 $\mu$M, and at 16 $\mu$M almost all the cells were dead. Duration of exposure does not significantly effect the cytotoxicity.

The preliminary data from one study in SKMel-28 cells indicate that fluoxetine is also toxic within the same range with the major toxicity range being 8–16 $\mu$M. Duration of exposure may have an effect on toxicity, but the results are to preliminary to make this conclusion with certainty. Interestingly, fluoxetine effects both pigmented and non-pigmented melanomas. The fact that fluoxetine is effective against two different metastatic tumor lines with differing pigmentation characteristics suggests that it could be universally effective for melanoma treatment.

EXAMPLE 6

Direct Application of Fluoxetine to Melanoma

Melanomas form initially in the dermis and are thus accessible to direct application of therapeutic agents. Fluoxetine can be incorporated in an ointment which can be applied topically to the melanoma or can be injected into the tumor site.

An ointment composition suitable for topical delivery in a penetration enhancer will include a sufficient amount of the fluoxetine to provide a level of fluoxetine in the tumor of approximately 100 to 300 ng/ml. Many compounds which enhance penetration of a drug through the skin are known. Fatty acids, fatty acid alcohols and other alcohols of about 12 carbon length have been found to be useful. Dimethylsufoxide is a particularly powerful penetrant enchancer. The formulation will be applied over the melanoma several times per day.

Transdermal patches may be a convenient method to apply fluoxetine once daily. Patches may be formed on a backing material by incorporating fluoxetine into a polyvinylpyrrolide polymer. The patch may have an adhesive around the edges for adherence to skin. Penetration enhancers may also be incorporated into the patches.

If the melanoma is not accessible to a topically applied composition, fluoxetine can be injected directly into the tumor. For this route of administration, fluoxetine is dissolved in a suitable saline solution, preferably isotonic saline, and injected directly into the tumor.

EXAMPLE 7

Fluoxetine as an Adjunct to Treatment with Antineoplastic Agents

Metastatic melanomas are not amenable to surgical extirpation and are routinely treated with chemotherapeutic drugs such as adriamycin, bleomycin, vinblastine, cis-platin and tamoxifen. Adjuncts such as interferon-alpha and interleukin-2 have also been tried. In general, response has not been good; melanomas that cannot be completely removed surgically are considered fatal. DTIC (dimethyltriazenoimidazole carboxymide) is considered to be the most effective single agent against melanoma. However, partial remissions have been accomplished in only about one-quarter of the cases of metastatic melanoma following treatment with DTIC. Therefore, chemotherapeutic drugs are generally used in combination. Because of the very low rates of long term remission, the goals of therapy in advanced melanoma are to minimize toxic effects of drugs, decrease the tumor burden, and to improve the psychological state of the patient.

Palliative relief such as that provided by the administration of fluoxetine may prolong life and improve the quality of life for these patients by slowing the growth of the tumors and counteracting weight loss, as well as by relieving depression. Fluoxetine may be administered by any of the routes noted above, even during the period chemotherapy is administered.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of inhibiting the growth of a melanoma cell comprising contacting the melanoma cell with an effective amount of a serotonin agent selected from the group consisting of fluoxetine, fluvoxamine, paroxetine, sertraline, and citalopram, and pharmaceutically acceptable salts thereof.

2. The method of claim 1 wherein the serotonin agent is fluoxetine or a pharmaceutically acceptable salt thereof.

3. The method of claim 1 wherein the melanoma cell is a pigmented cell.

4. The method of claim 1 wherein the melanoma cell is a non-pigmented cell.

5. A method for the treatment of melanoma in a mammal, which method comprises administering to said mammal an effective anti-melanoma amount of a serotonin agent selected from the group consisting of fluoxetine, fluvoxamine, paroxetine, sertraline, and citalopram, and pharmaceutically acceptable salts thereof.

6. The method of claim 5, wherein the serotonin agent is administered orally, subcutaneously, topically, or intravenously.

7. The method of claim 5 wherein the serotonin agent is fluoxetine or a pharmaceutically acceptable salt thereof.

8. The method of claim 5, wherein the mammal is a human.

9. A method of inhibiting metastasis of melanoma in a mammal, comprising administering to said mammal an effective metastasis-inhibiting amount of a serotonin agent selected from the group consisting of fluoxetine, fluvoxamine, paroxetine, sertraline, and citalopram, and pharmaceutically acceptable salts thereof.

10. The method of claim 9, wherein the serotonin agent is administered orally, subcutaneously, topically, or intravenously.

11. The method of claim 9, wherein the serotonin agent is fluoxetine or a pharmaceutically acceptable salt thereof.

12. The method of claim 9, wherein the mammal is a human.

* * * * *

UNITED STATES PATENT AND TRADEMARK OFFICE
CERTIFICATE OF CORRECTION

PATENT NO. : 6,927,223 B1
DATED : August 9, 2005
INVENTOR(S) : Meadows et al.

It is certified that error appears in the above-identified patent and that said Letters Patent is hereby corrected as shown below:

Title page,
Item [56], References Cited, OTHER PUBLICATIONS,
"Carter et al." reference, after "N.Y.," delete "N.Y.,".
Delete "Iken, K.et al.," and insert -- Iken, K., et al., --, therefor.
"Iken, K. et al." reference, delete "Stimuilated" and insert -- Stimulated --, therefor.
"Stewart W. Clarks et al." reference, delete "Clarks" and insert -- Clarke --, therefor.

Signed and Sealed this

Twenty-ninth Day of November, 2005

JON W. DUDAS
*Director of the United States Patent and Trademark Office*